US007601735B2

(12) United States Patent
Tyms et al.

(10) Patent No.: US 7,601,735 B2
(45) Date of Patent: Oct. 13, 2009

(54) ANTIVIRAL COMPOUNDS (75) Inventors: Albert Stanley Tyms, London (GB);
Debra Lynn Taylor, London (GB)

(73) Assignee: Virogen Ltd., London (GB)

( * ) Notice: Subject to any disclaimer, the term of this patent is extended or adjusted under 35 U.S.C. 154(b) by 649 days.

(21) Appl. No.: 10/475,830

(22) PCT Filed: May 2, 2002

(86) PCT No.: PCT/EP02/04944

§ 371 (c)(1),
(2), (4) Date: Mar. 9, 2004

(87) PCT Pub. No.: WO02/089780

PCT Pub. Date: Nov. 14, 2002

(65) Prior Publication Data
US 2004/0147549 A1    Jul. 29, 2004

(30) Foreign Application Priority Data
May 3, 2001    (GB)    ................................. 0110832.3

(51) Int. Cl.
*A61K 31/44* (2006.01)
*A61K 38/00* (2006.01)
*A61K 31/70* (2006.01)

(52) U.S. Cl. ........................... 514/299; 514/12; 514/43; 514/894

(58) Field of Classification Search .................. 514/299, 514/894
See application file for complete search history.

(56) References Cited

U.S. PATENT DOCUMENTS

| 4,849,430 A | 7/1989 | Fleet et al. |
| 4,970,317 A | 11/1990 | Margolin et al. ............. 546/112 |
| 5,004,746 A | 4/1991 | Liu et al. ..................... 514/299 |
| 5,066,807 A | 11/1991 | Anzeveno et al. ........... 546/183 |
| 5,093,501 A | 3/1992 | Anzeveno et al. ........... 548/526 |
| 5,385,911 A | 1/1995 | Sunkara et al. ............. 514/299 |
| 5,939,430 A | 8/1999 | Tyms et al. ................. 514/299 |
| 5,959,111 A | 9/1999 | Goralski et al. ............. 546/183 |

FOREIGN PATENT DOCUMENTS

| EP | 297534 B1 | 12/1994 |
| WO | WO 99/29321 | 6/1999 |
| WO | WO 01/54692 | 8/2001 |

OTHER PUBLICATIONS

Michael, Joseph P., "Indolizidine and Quinolizidine Alkaloids," *Natural Product Reports*, 1997, p. 619-636.
Norwegian Office Action dated Feb. 22, 2007, which issued for Norwegian Patent Application No. 20034878.
Dubuisson, J. et al., "Glycosylation of the Hepatitis C Virus Envelope Protein E1 Is Dependent on the Prescence of a Downstream Sequence on the Viral Polyprotein," *The Journal of Biological Chemistry* 275(39): 30605-30609, 2000.

(Continued)

*Primary Examiner*—Shengjun Wang
(74) *Attorney, Agent, or Firm*—Foley & Lardner LLP (57) ABSTRACT Use of certain castanospermine esters in the treatment of diseases caused by flaviviruses, in particular in the treatment of disease caused by the hepatitis C virus (HCV) and compositions containing said esters in combination with adjunctive therapeutic agents.

12 Claims, 3 Drawing Sheets

Comparison of the anti-BVDV activity of Bucast and castanospermine by plaque reduction assay in MDBK cells

OTHER PUBLICATIONS

Dubuisson and Rice, "Hepatitis C Virus Glycoprotein Folding: Disulfide Bond Formation and Association with Calnexin," *Journal of Virology 70*(2): 778-786, Feb. 1996.

Chan-Fook, C. et al., "Hepatitis C Virus Glycoprotein E2 Binding to CD81: The Role of E1E2 Cleavage and Protein Glycosylation in Bioactivity," *Virology 273*(1): 60-66, Jul. 20, 2000.

Meunier, J-C. et al., "Analysis of the glycosylation sites of hepatitis C virus (HCV) glycoprotein E1 and the influence of E1 glycans on the formation of the HCV glycoprotein complex," *Journal of General Virology 80*:887-896, 1999.

Blight, K.J. et al., "Molecular virology of hepatitis C virus: an update with respect to potential antiviral targets," *Antiviral Therapy 3*(Supplement 3): 71-81, 1998.

Dubuisson, J. et al., "Assembly of Hepatitis C virus glycoproteins," *Recent Research Developments in Virology*, vol. 1, Part 1, Pandalai, S.G. (ed.), Transworld Research Network, Trivandrum, India, 1999, pp. 29-39.

Ruprecht, R.M. et al., "In Vivo Analysis of Castanospermine, a Candidate Antiretroviral Agent," *Journal of Acquired Immune Deficiency Syndromes 2*(2): 149-157, 1989.

Sunkara, P.S. et al., "Inhibition of Glycoprotein Processing and HIV Replication by Castanospermine Analogues," *Annals of the New York Academy of Sciences 616*: 90-96, 1990.

Dettenhofer and Yu, "Characterization of the Biosynthesis of Human Immunodeficiency Virus Type 1 Env from Infected T-cells and the Effects of Glucose Trimming of Env on Virion Infectivity," *The Journal of Biological Chemistry 276*(8): 5985-5991, Feb. 23, 2001.

Ahmed, S.P. et al., "Antiviral Activity and Metabolism of the Castanospermine Derivative MDL 28,574, in Cells Infected with Herpes Simplex Virus Type 2," *Biochemical and Biophysical Research Communications 208*(1): 267-273, Mar. 8, 1995.

Bridges, C.G. et al., "The effect of oral treatment with 6-*O*-butanoyl castanospermine (MDL 28,574) in the murine zosteriform model of HSV-1 infection," *Glycobiology 5*(2): 249-253, 1995.

Zitzmann, N. et al., "Imino sugars inhibit the formation and secretion of bovine viral diarrhea virus, a pestivirus model of hepatitis C virus: Implications for the development of broad spectrum anti-hepatitis virus agents," *Proc. Natl. Acad. Sci. USA 96*(21): 11878-11882, Oct. 12, 1999.

Block, et al., PNAS 91:2235-2239) (1994), "*Secretion of Human Hepatitis B Virus is Inhibited by the Imino Sugar N-butyldeoxynojirimycin*".

Blough, et al. Biochemical and Biophysical Research Communications (141(1), 33-38 (1986), "*Glycosylation Inhibitors Block the Expression of LAV/HTLV-III (HIV) Glycoproteins*".

McDowell, et al., Biochemistry, 34(27), 8145-52 (1985), "*Mechanism of Inhibition of Protein Glycosylation by the Antiviral Sugar Analogue 2-Deoxy-2-fluoro-D-mannose: Inhibition of Synthesis of Man(GlcNAc)$_2$—PP Dol by the Guanosine Diphosphate Ester*".

Lu, et al., Virology 213:660-665 (1995), "*Evidence that the N-Linked Glycosylation is Necessary for Hepatitis B Virus Secretion*".

Sunkara, et al., Lancet II 1206 (1989), "*Anti-HIV Activity of Castanospermine Analogues*".

Kang et al.; Castanospermine analogues: their inhibition of glycoprotein processing α-glucosidases from porcine kidney and $B_{16}F_{10}$ cells; Glycobiology; 1995; 147-152; Oxford University Press.

Kang, "Uptake and metabolism of BuCast: a glycoprotein processing inhibitor and a potential anti-HIV drug," *Glycobiology 6*(2): 209-216, 1996.

Taylor et al., Antiviral Res. 10:11-26 (1988), "*Loss of Cytomegalovirus Infectivity After Treatment with Castanospermine . . .*".

Taylor et al., Antimicrob. Ag. Chemother. 38:1780-1787 (1994), "*Inhibition of α-Glucosidase I of the Glycoprotein-Processing Enzymes . . .*".

Branza-Nichita et al., J. Virol. 75(8):3527-3536 (2001), "*Antiviral Effect of N-Butyldeoxynojirimycin against Bovine Viral Diarrhea . . .*".

Courageot et al., J. Virol. 74(1):564-572 (2000), "*α-Glucosidase Inhibitors Reduce Dengue Virus Production by Affecting the Initial Steps of Virion Morphogenesis . . .*".

Choukhi et al., J. Virol., 72(5):3851-3858 (1998), "*Involvement of Endoplasmic Reticulum Chaperones in the Folding of Hepatitis C Virus Glycoproteins*".

Figure 1

Comparison of the anti-BVDV activity of Bucast and castanospermine by plaque reduction assay in MDBK cells

Figure 2

Anti-BVDV activity and cytotoxicity of α-glucosidase I
inhibitors determined by XTT cytopathicity assay

Anti-BVDV activity of Bucast and N-butyl-DNJ at different multiplicities of infection as determined by XTT cytopathicity assay

ANTIVIRAL COMPOUNDS

FIELD OF THE INVENTION

The present invention relates to the use of certain castanospermine esters in the treatment of diseases caused by flaviviruses, in particular in the treatment of disease caused by the hepatitis C virus (HCV).

BACKGROUND TO THE INVENTION

Flaviviruses

The flavivirus group (family Flaviviridae) comprises the genera *Flavivirus*, *Pestivirus* and *Hepacivirus* and includes the causative agents of numerous human diseases and a variety of animal diseases which cause significant losses to the livestock industry.

The family Flavivirdae (members of which are referred to herein as flaviviruses) include the genera *Flavivirus* (e.g. yellow fever virus, dengue viruses, Japanese encephalitis virus and tick-borne encephalitis virus), Pestivirus (e.g. bovine viral diarrhoea virus, classical swine fever virus and border disease virus), *Hepacivirus* (hepatitis C virus) and currently unclassified members of the Flaviviridae (e.g. GB virus types A, B and C).

The full list of members of the Flaviviridae are defined in detail by the International Committee on Taxonomy of Viruses (the currently accepted taxanomic definition is described in: Virus Taxonomy: The Classification and Nomenclature of Viruses. The Seventh Report of the International Committee on Taxonomy of Viruses (book). M. H. V. van Regenmortel, C. M. Fauquet, D. H. L. Bishop, E. B. Carstens, M. K. Estes, S. M. Lemon, J. Maniloff, M. A. Mayo, D. J. McGeoch, C. R. Pringle, R. B. Wickner (2000). Virus Taxonomy, VIIth report of the ICTV. Academic Press, San Diego), the contents of which are hereby incorporated by reference.

However, perhaps the most significant flavivirus is the hepatitis C virus (HCV). HCV was first identified in 1989 and it has since become clear that this virus is responsible for most cases of post-transfusion non-A, non-B hepatitis. Indeed, HCV is now recognised as one of the commonest infections causing chronic liver disease and The World Health Organisation estimates that 170 million people are chronically infected. HCV infection results in a chronic infection in 85% of infected patients and approximately 20-30% of these will progress to cirrhosis and end stage liver disease, frequently complicated by hepatocellular carcinoma.

The study of HCV has been hampered by the inability to propagate the virus efficiently in cell culture. However, in the absence of a suitable cell culture system able to support replication of human HCV, BVDV is an accepted cell culture model. HCV and BVDV share a significant degree of local protein homology, a common replication strategy and probably the same subcellular location for viral envelopment.

HCV is an enveloped plus-strand RNA virus belonging to the Flaviviridae family, but classified as a distinct genus *Hepacivirus*. The HCV genome consists of a single long open reading frame which encodes a ~3000 amino acid residue polyprotein. This polyprotein is processed co- and post translationally into at least 10 different products including two N-linked glycosylated proteins E1 and E2.

The genome carries at the 5' and 3' ends non-translated regions (NTRs) that form stable secondary and tertiary structures. The 5' NTR carries an internal ribosome entry site (IRES) permitting the direct binding of ribosomes in close proximity to the start codon of the ORF. Thus translation of HCV RNA is mediated by the IRES, rather than the CAP-dependent mechanism typically used by cellular mRNA.

Within the polyprotein, cleavage products are ordered as follows: core (C), envelope protein 1 (E1), E2, p7, non-structural protein 2(NS2), NS3, NS4A, NS4B, NS5A and NS5B. The core protein is a highly basic RNA binding protein forming the major constituent of the nucleocapsid. The envelope proteins E1 and E2 are highly glycosylated type 1 membrane proteins anchored through the carboxy-terminal region. They are embedded into the lipid envelope of the virus particle and associate to form stable heterodimers. The cleavage product p7 is a small hydrophobic peptide of unknown function. The non-structural proteins are involved in viral replication and possess protease (NS2/NS3), helicase (NS3) and RNA polymerase activities (NS5B).

Binding to the host cell probably requires the interaction of E2 or the E1/E2 complex with a receptor that is present on the cell surface.

Due to the lack of an efficient cell culture replication system the understanding of HCV particle assembly is very limited. However, the absence of complex glycans, the localisation of expressed HCV glycoproteins in the endoplasmic reticulum (ER) and the absence of these proteins on the cell surface suggest that initial virion morphogenesis occurs by budding into intracellular vesicles from the ER. Additionally, mature E1-E2 heterodimers do not leave the ER, and ER retention signals have been identified in the C-terminal regions of both E1 and E2. In this case the virus would be exported via the constitutive secretory pathway. In agreement with this assumption, complex N-linked glycans were found on the surface of partially purified virus particles suggesting that the virus transits through the Golgi.

Until recently, interferon-α(IFN-α) was the only therapy with proven benefit for the treatment of HCV infection. Using IFN-αup to 50% of patients show a response to treatment, but this is not sustainable in the majority of patients and there are considerable associated side effects. More recently, greater success has been achieved using IFN-αin combination with the nucleoside analogue ribavirin, but continuing research is required to identify new therapeutic candidates that will have more potent antiviral activity and less severe side-effects.

There is therefore a need for improved anti-flaviviral drugs in general, and anti-HCV drugs in particular.

Glycoproteins and viral development

Glycoproteins are classified into two major classes according to the linkage between sugar and amino acid of the protein. The most common and extensively studied is N-glycosidic linkage between an asparagine of the protein and an N-acetyl-D-glucosamine residue of the oligosaccharide. N-linked oligosaccharides, following attachment to a polypeptide backbone, are processed by a series of specific enzymes in the endoplasmic reticulum (ER) and this processing pathway has been well characterised.

In the ER, α-glucosidase I is responsible for the removal of the terminal α-1,2 glucose residue from the precursor oligosaccharide and α-glucosidase II removes the two remaining α-1,3 linked glucose residues, prior to removal of mannose residues by mannosidases and further processing reactions involving various transferases. These oligosaccharide "trimming" reactions enable glycoproteins to fold correctly and to interact with chaperone proteins such as calnexin and calreticulin for transport through the Golgi apparatus.

Inhibitors of key enzymes in this biosynthetic pathway, particularly those blocking α-glucosidases and α-mannosidase, have been shown to prevent replication of several enveloped viruses. Such inhibitors may act by interfering with the folding of the viral envelope glycoprotein, so preventing the initial virus-host cell interaction or subsequent fusion. They may also prevent viral duplication by preventing the construction of the proper glycoprotein required for the completion of the viral membrane.

For example, it has been reported that the nonspecific glycosylation inhibitors 2-deoxy-D-glucose and β-hydroxy-norvaline inhibit expression of HIV glycoproteins and block the formation of syncytia (Blough et al., Biochemical and Biophysical Research Communications, 141(1), 33-38 (1986)). Viral multiplication of HIV-infected cells treated with these agents is stopped, presumably because of the unavailability of glycoprotein required for viral membrane formation.

In another report, the glycosylation inhibitor 2-deoxy-2-fluoro-D-mannose was found to exhibit antiviral activity against influenza infected cells by preventing the glycosylation of viral membrane protein (McDowell et al., Biochemistry, 24(27), 8145-52 (1985)). This report also studied the antiviral activity of 2-deoxyglucose and 2-deoxy-2-fluoroglucose and found that each inhibits viral protein glycosylation by a different mechanism.

Lu et al (1995) present evidence that N-linked glycosylaton is necessary for hepatitis B virus secretion (Virology 213: 660-665) while Block et al (1994) show that secretion of human hepatitis B virus is inhibited by the imino sugar N-butyldeoxynojirimycin (PNAS 91: 2235-2239). See also WO9929321.

Taylor et al (1988) demonstrate the loss of cytomegalovirus infectivity after treatment with castanospermine or other plant alkaloids and relate this to abberant glycoprotein synthesis (Antiviral Res. 10: 11-26). See also U.S. Pat. No. 5,004,746.

Taylor et al. (1994) show that inhibition of α-glucosidase I of the glycoprotein processing enzymes by 6-0-butanoyl castanospermine has consequences in human immunodeficiency virus-infected T-cells (Antimicrob. Ag. Chemother. 38: 1780-1787) while Sunkara et al (1989) describe anti-HIV activity of castanospermine analogues (Lancet II 1206). See also U.S. Pat. No. 5,004,746.

U.S. Pat. No. 5,385,911 discloses anti-herpes activity in certain castanospermine esters.

However, many other known glycosylation inhibitors have been found to have no antiviral activity. Thus the antiviral activity against enveloped viruses, in general, and the antiflaviviral activity, specifically, of glycosylation inhibitors is quite unpredictable.

Glucosidase Inhibitors

Castanospermine and certain imino sugars, such as deoxynojirimycin (DNJ), are ER α-glucosidase inhibitors and both potently inhibit the early stages of glycoprotein processing. However, their effects differ substantially depending on the system to which they are applied and they may exhibit quite different specificities, castanospermine being relatively specific for α-glucosidase I.

Castanospermine is an alkaloid, originally isolated from the seeds of *Castanospermum australe*, having the following formula:

Systematically, this compound can be named in several ways as follows: [1S-(1α, 6β,7α,8β,8αβ)]-octahydro-1,6,7, 8-indoli-zinetetrol or [(1S,(1S,6S,7R,8R,8aR)-1,6,7,8-tetrahydroxy-indolizidine or 1,2,4,8-tetradeoxy-1,4,8-nitrilo-L-glycero-D-galacto-octitol. The term "castanospermine" or the first systematic name will be used in the discussion below.

Branza-Nichita et al. (2001) J. Virol 75(8): 3527-3536 show that the Iminosugar N-butyldeoxynojirimycin has an antiviral effect against the Pestivirus B VDV. However, the authors make clear that while treatment with α-glucosidase inhibitors may affect the life cycles of this and other enveloped viruses, it is not possible to generalize to other viruses since the effects may depend crucially on the particular folding pathway used by the viral proteins.

Courageot et al. (2000) J. Virol. 74(1): 564-572 report that the α-glucosidase inhibitors castanospermine and DNJ reduce dengue virus production in an in vitro mouse model. However, no substantial difference in activity between the imino sugar inhibitor DNJ and castanospermine was reported.

WO 99/29321 discloses the use of α-glucosidase inhibitors generally (and imino sugars in particular) in the treatment of inter alia HCV infections. However, no reference is made to castanospermine (or esters or derivatives thereof) specifically in this respect. Instead, the document focuses on the activities of various imino sugars.

Choukhi et al. (1998) J. Virol. 72(5): 3851-3858 report the effect of castanospermine on the interactions between HCV glycoproteins and their chaperones. Castanospermine did not abolish the interaction between HCV glycoproteins and the chaperones calnexin and calreticulin. Rather, castanospermine actually increased the binding of the glycoproteins to calreticulin. The authors suggest that HCV glycoprotein processing may not be sensitive to inhibitors of glycoprotein trimming (such as castanospermine), concluding that:

. . . binding of HCV glycoproteins to and release from calnexin or calreticulin could be independent of trimming . . . of the N-linked glycans.

[Choukhi et al., page 3856, column 1]

Despite such contra-teachings, the present inventors have now surprisingly discovered that certain esters of castanospermine do in fact exhibit antiviral activity against members of the Flaviviridae (including HCV). Moreover, they have found that the therapeutic index is unexpectedly far superior to that exhibited by other α-glucosidase inhibitors of the imino sugar class (the esters exhibit relatively high antiviral activity and relatively low toxicity). Without wishing to be bound by any theory, it is postulated that these unexpected properties of the castanospermine esters may reflect their relative specificity for a particular class of glycoprotein processing enzymes (viz. α-glucosidase I).

SUMMARY OF THE INVENTION

According to the present invention there is provided a method for treating a flavivirus infection in a patient in need thereof which comprises administering to the patient an effective amount of a castanospermine ester of the formula:

wherein R, R₁ and R₂ are independently hydrogen, $C_{1-14}$ alkanoyl, $C_{1-14}$ alkenoyl, cyclohexanecarbonyl, $C_{1-4}$ alkoxyacetyl, naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by $C_{1-10}$ alkyl; thiophenecarbonyl optionally substituted by methyl or halogen; or furancarbonyl optionally substituted by methyl or halogen; Y is hydrogen. $C_{1-4}$ alkyl, $C_{1-4}$ alkoxy, halogen, trifluoromethyl, $C_{1-4}$ alkylsulphonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; with R, R₁ and R₂ being selected in such a way that at least one of them, but not more than two of them, is hydrogen; or a pharmaceutically acceptable salt or derivative thereof.

Preferably, R, R₁ and R₂ are each independently hydrogen, $C_{1-10}$ alkanoyl, $C_{1-10}$ alkenoyl, $C_{1-8}$ alkoxyacetyl, or wherein Y is hydrogen, $C_{1-4}$ alkyl, $C_{1-4}$ alkoxy, halogen, trifluoromethyl, $C_{1-4}$ alkylsulphonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkoxy or halogen; with R. R₁ and R₂ being selected In such a way that at least one of them, but not more than two of them, is hydrogen.

R, R₁ and R₂ may each be independently hydrogen, $C_{1-8}$ alkanoyl, $C_{1-8}$ alkenoyl, $C_{1-8}$ alkoxy-acetyl, or a benzoyl optionally substituted with an alkyl or halogen; with R, R₁ and R₂ optionally being selected in such a way that at least one of them, but not more than two of them, is hydrogen.

R, R₁ and R₂ may each be independently hydrogen, $C_{1-8}$ alkanoyl, $C_{1-8}$ alkenoyl, $C_{1-8}$ alkoxy-acetyl, or a benzoyl optionally substituted with a methyl, bromo, chloro, or fluoro group; with R, R₁ and R₂ optionally being selected in such a way that at least one of them, but not more than two of them, is hydrogen.

In preferred embodiments the castanospermine esters have the structures shown in Table 1.

| Compound | Structure R | Compound | Structure R |
|---|---|---|---|
| CAST | H | MDL 29270 | H |
| MDL 28574 | CH₃(CH₂)₂—CO | MDL 44370 | Br—⌬—CO—: |
| MDL 43305 | ⌬—CO— | MDL 29797 | CH₃(CH₂)₆—CO— |
| MDL 28653 | furan—CO— | MDL 29710 | CH₃(CH₂)₃—CO— |
| MDL 29435 | H₃C-⌬—CO— (meta) | MDL 29513 | CH₃CH₂(CH)₂CH₂—CO— |
| MDL 29204 | H₃C—⌬—CO— | | |

* In MDL 29270 R₁ is in all other structures R₁ is H

Basic Structure

Particularly preferred are castanospermine esters wherein R₁ is a $C_{1-8}$ alkanoyl, $C_{1-0}$ alkenoyl, $C_{1-8}$ alkoxy-acetyl, or a benzoyl optionally substituted with an alkyl or halogen group.

R₁ may be a $C_{1-8}$ alkanoyl, $C_{1-8}$ alkenoyl, $C_{1-8}$ alkoxyacetyl, or a benzoyl optionally substituted with a methyl, bromo, chloro, or fluoro group.

The castanospermine ester may be selected from:
(a) [1 S-(1α,6β,7α,8β,8αβ)]-octahydro-1,6,7,8-indolizinetetrol 6-benzoate;
(b) [1S-(1 α,6β,7α,8β,8αβ)]-octahydro-1,6,7,8-indolizinetetrol 7-benzoate;
(c) [1 S-(1α,6β,7α,8β,8αβ)]-octahydro-1,6,7,8-indolizinetetrol 6-(4-methylbenzoate);
(d) [1 S-(1α,6β, 7α,8β,8αβ)]-octahydro-1,6,7,8-indolizinetetrol 7-(4 bromobenzoate);
(e) [1 S-(1α,6β7α,8β,8αβ)]-octahydro-1,6,7,8-indolizinetetrol 6,8-dibutanoate;
(f) [1 S—(1α,6β,7α, 8β,8αβ)]-octahydro-1,6,7,8-indolizinetetrol 6-butanoate;
(g) [1 S-(1α,6β,7α,8β,8αβ)]-octahydro-1,6,7,8-indolizinetetrol 6-(2-furancarbonxylate);
(h) [1 S-(1α,6β,7α,8β,8αβ)]-octahydro-1,6,7,8-indolizinetetrol 7-(2,4-dichlorobenzoate);
(i) [1S-(1 α,6β,7α,8β,8αβ)]-octahydro-1,6,7,8-indolizinetetrol 6-(3-hexenoate);
(j) [1S-(1α,6β,7α,8β,8αβ)]-octahydro-1,6,7,8-indolizinetetrol 6-octanoate;
(k) [1S-(1α,6β,7α,8β,8αβ)]-octahydro-1,6,7,8-indolizinetetrol 6-pentanoate;
(l) an O-pivaloyl ester;
(m) a 2-ethyl-butyryl ester;
(n) a 3,3-dimethylbutyryl ester;
(o) a cyclopropanoyl ester;
(p) a 4-methoxybenzoate ester;
(q) a 2-aminobenzoate ester; and
(r) a mixture of any or all of (a)-(q).

The flavivirus may for example be a member of the genus *Pestivirus* or *Flavivirus*.

In preferred embodiments, the flavivirus is a member of the genus *Hepacivirus*. In a particularly preferred embodiment the Hepacivirus is the hepatitis C virus (HCV).

Other flaviviruses include include members of the genera *Flavivirus* (e.g. yellow fever virus, dengue viruses, Japanese encephalitis virus and tick-borne encephalitis virus), *Pestivirus* (e.g. bovine viral diarrhoea virus, classical swine fever virus and border disease virus and currently unclassified members of the Flaviviridae (e.g. GB virus types A, B and C)

In another aspect of the invention, the flavivirus is an animal virus, for example a Pestivirus optionally selected from bovine diarrhoea virus (BVDV), classical swine fever virus, border disease virus and hog cholera virus.

In another aspect of the invention there is provided the use of a castanospermine ester as described above for the manufacture of a medicament for use in the therapy or prophylaxis of a flavivirus infection.

Thus, the invention contemplates a process for the manufacture of a medicament for use in the therapy or prophylaxis of a flavivirus infection, characterized in the use (e.g. as an active ingredient) of the castanospermine esters described above.

The therapy or prophylaxis is preferably the treatment or prevention of an infection by a virus as defined above. In particular, the therapy or prophylaxis may be the treatment or prevention of a disease selected from hepatitis C, yellow fever, dengue fever, Japanese encephalitis, Murray Valley encephalitis, Rocio virus infection, West Nile fever, St. Louis encephalitis, tick-borne encephalitis, Louping ill virus infection, Powassan virus infection, Omsk hemorrhagic fever, Kyasanur forest disease, bovine diarrhoea, classical swine fever, border disease and hog cholera.

The pharmaceuticals of the invention may also comprise the castanospermine esters of the invention in association (e.g. in admixture or co-packaged with) an adjunctive therapeutic. The adjunctive therapeutic may comprise an antiviral compound, for example an anti-HCV drug. Particularly preferred are adjunctive therapeutics comprising interferon-α and/or ribavirin.

Thus, in another aspect, the invention provides a composition comprising a castanospermine ester as defined in any one of the preceding claims in combination with: (a) compounds which inhibit the binding to and/or infection of cells by HCV. These include antibodies (e.g. monoclonal antibodies) against, for example, HCV E1 and/or E2 proteins) and glucosaminoglycans (such as heparan sulphate and suramin); (b) compounds which Inhibit the release of viral RNA from the viral capsid or the function of HCV gene products, including inhibitors of the IRES, protease (e.g. serine protease) inhibitors, helicase inhibitors and inhibitors of the viral polymerase/replicase; (c) compounds which perturb cellular functions involved in or influencing viral replication, Including inhibitors of inosine monophosphate dehydrogenase (e.g. Ribavirin, mycophenolic acid and VX497) and inhibitors of glycoprotein processing such as DNJ and its derivatives; (d) compounds which act to alter immune function (e.g. thymosin alpha and interferons such as a interferons and β interferons) and (e) compounds which act to modulate the symptoms and effects of HCV infection (e.g. antioxidants such as the flavinoids).

In addition the invention provides a composition comprising a castanospermine ester as defined in any one of the previous claims in combination with compounds used in the treatment of frequently found co-infections (such as hepatitis B virus and the human retroviruses such as human immunodeficiency viruses types 1 and 2 and human T-cell lymphotrophic viruses types 1 and 2). Examples of such compounds include nucleotide RT inhibitors (e.g. Lamivudine (3TC), zidovudine, stavudine, didanosine, adefovir dipivoxil and abacavir), non-nucleoside RT inhibitors (e.g. nevirapine) and and protease inhibitors (e.g. saquinavir, indinavir and ritonavir).

The adjunctive therapeutics discussed above can be administered together with the castanospermine esters of the invention. Alternatively the castanospermine esters and adjunctive therapeutic(s) can be sequentially administered.

Preferably, the interferon is interferon-α (IFN-α), though other interferons may also be used (for example an interferon produced by expression of a cloned human interferon gene).

The composition described above optionally further comprises a pharmaceutically acceptable excipient. Thus, the invention also contemplates a pharmaceutical composition comprising the composition described above.

The composition of the invention is preferably for use in therapy or prophylaxis, for example in any of the therapeutic and prophylactic methods described herein.

In another aspect, the invention provides a pharmaceutical kit of parts comprising a castanospermine ester as defined in any one of the preceding claims in combination with: (a) compounds which inhibit the binding to and/or infection of cells by HCV; (b) compounds which inhibit the release of viral RNA from the viral capsid or the function of HCV gene products; (c) compounds which perturb cellular functions involved in or influencing viral replication; (d) compounds which act to alter immune function, and (a) compounds which act to modulate the symptoms and effects of HCV infection, as described above.

The kit may also further comprise instructions for use in the treatment of a flaviviral disease (for example in the flaviviral diseases described herein).

The castanospermine ester and adjunctive therapeutic agent(s) may be co-packaged in unit dosage form.

In the compositions of the invention the castanospermine ester and the adjunctive therapeutic(s) may act in a complementary or synergistic fashion.

Particularly preferred are compositions and methods comprising both the castanospermine esters of the invention and interferon which act in a synergistic fashion in the treatment of HCV infection.

In any of the foregoing pharmaceutical compositions, the composition or castanospermine esters of the invention may be present in unit dosage form.

Thus the invention also contemplates a kit as defined above in which the castanospermine ester and the adjunctive therapeutic(s) are in unit dosage form.

DETAILED DESCRIPTION OF THE INVENTION

As used herein, the term "flavivirus" is intended to cover any member of the Flavivirdae family.

The expression "a pharmaceutically acceptable salt" is intended to cover any non-toxic organic or inorganic acid addition salt of the base compounds.

Illustrative inorganic acids which form suitable salts include hydrochloric, hydrobromic, sulphuric, and phosphoric acids and acid metal salts such as sodium monohydrogen orthophosphate and potassium hydrogen sulphate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulphonic acids such as methane sulphonic acid and 2-hydroxyethane sulphonic acid.

These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution.

In general the acid addition salts of the compounds of this invention are crystalline materials which are soluble in water and various hydrophilic organic solvents and which in comparison to their free base forms, demonstrate higher melting points and an increased solubility.

The expression "a pharmaceutically acceptable derivative" is intended to cover ester pro-drugs which have greater resistance to hydrolysis and increased lipophilicity. Such pro-drugs exhibit rapid removal from the GI tract when delivered orally whilst providing a "depot effect" which sustains the concentration of the active drug at the target site (e.g. the liver).

The $C_{1-14}$ alkanoyl groups referred to above can be straight- or branched-chain or cyclic and can be exemplified by formyl, acetyl, propionyl, butyryl, isobutyryl, cyclopropanecarbonyl, hexanoyl, octanoyl and decanoyl.

The $C_{1-14}$ alkenoyl groups referred to above can be straight- or branched-chain or cyclic but have at least one carbon-carbon double bond. Examples include propenoyl, butenoyl, isobutenoyl, hexenoyl, octenoyl and decenoyl.

The $C_{1-6}$ alkoxyacetyl referred to above can be methoxyacetyl, ethoxyacetyl and butoxyacetyl.

The halogens referred to above can be exemplified by fluorine, chlorine, bromine or iodine.

The $C_{2-6}$ alkanoyl groups referred to above can be acetyl, propionyl, butyryl, isobutyryl and hexanoyl.

The $C_{1-4}$ alkyl groups referred to above, whether alone or as part of an alkoxy, an alkylsulphonyl or an alkyl-mercapto group, can be straight- or branched-chain alkyl groups containing up to 4 carbon atoms. Examples of various such groups are methyl, ethyl, propyl, butyl, methoxy, ethoxy, butoxy, methylsulphonyl, ethylsulphonyl, methylmercapto and ethylmercapto.

The phenyl ($C_{2-6}$ alkanoyl) groups referred to above can be benzeneacetyl and benzenepropionyl.

The various naphthalenecarbonyl, pyridinecarbonyl, thiophenecarbonyl and furancarbonyl groups referred to above include the various position isomers and these can be naphthalene-1 carbonyl, naphthalene2-carbonyl, nicotinoyl, isonicotinoyl, N-methyl-dihydro-pyridine-3-carbonyl, thiophene-2-carbonyl, thiophene-3-carbonyl, furan-2-carbonyl and furan-3-carbonyl. The naphthalene, pyridine, thiophene and furan groups can be optionally further substituted as indicated above.

Preferred compounds of the present invention are those wherein R, $R_1$ and $R_2$ are 1 or 2 alkanoyl, alkenoyl, or benzoyl groups with the benzoyl substituted by Y, Y' and Y" as described above, especially a $C_{1-4}$ alkanoyl or a benzoyl optionally substituted with an alkyl or halogen.

More preferred are those compounds of formula 1 wherein one of R, $R_1$ and $R_2$ is alkanoyl or benzoyl, especially a $C_{1-8}$ alkanoyl, $C_{1-8}$ alkenoyl, or a benzoyl optionally substituted with an alkyl or halogen, and the others are hydrogens.

Even more preferred are those compounds of formula 1 wherein one of R, $R_1$ and $R_2$ is a $C_{1-8}$ alkanoyl, $C_{1-8}$ alkenoyl, or a benzoyl optionally substituted with an alkyl or halogen, especially a methyl, bromo, chloro, or fluoro group, and the others are hydrogens.

Most preferred are those compounds of formula 1 wherein $R_1$ is a $C_{1-8}$ alkanoyl, $C_{1-8}$ alkenoyl, or benzoyl optionally substituted with an alkyl or halogen, especially a methyl, bromo, chloro, or fluoro group, most especially a methyl, bromo, chloro, or fluoro group at the para position, and wherein R and $R_2$ are each a hydrogen.

The esters of the present invention are prepared by the reaction of castanospermine with an appropriate acid chloride or anhydride in an inert solvent. The halide can be a chloride or bromide and the anhydride includes mixed anhydrides. The relative amount of the acid halide or anhydride used, the relative amount of solvent, the temperature and the reaction time are all controlled so as to minimize the number of hydroxy groups that will be acylated. Thus, only a limited 
excess of the acid derivative is used, which means up to about a three-fold excess of the acylating agent.

Use of a solvent in relatively large amounts, serves to dilute the reactants and suppress the amount of higher acylated products that form. The solvent used is preferably one that will dissolve the reactants used without reacting with them.

It is further preferable to carry out the reaction in the presence of a tertiary amine which will react with and remove any acid formed during the course of the reaction. The tertiary amine can be added to the mixture or it can itself be used in excess and serve as the solvent. Pyridine is a preferred solvent in this regard. As indicated above, the time and the temperature are likewise controlled to limit the amount of acylation that takes place.

Preferably, the reaction is carried out with cooling in an ice-bath for a period of about 16 hours to give the monoesters with the reaction time extended to a longer period, such as 7 days, if diesters are desired. The reaction can actually be carried out at higher temperatures and heating can be used as long as the various factors involved are properly controlled.

When the reaction is carried out as described, the final reaction mixture will still contain a considerable amount of unreacted castanospermine. This unreacted material can be recovered from the reaction mixture and recycled in subsequent reactions and thus increase the overall amount of castanospermine converted to ester. This recycling is particularly important when the reaction is carried out under conditions which would favor the isolation of monoesters.

The procedures as described above will generally give 6-or 7-monoesters or 6,7- or 6,8-diesters. Other isomers can be obtained by appropriate use of blocking groups. Thus, for example, castanospermine can be reacted with 2-(dibromomethyl)benzoyl chloride to give the 6,7-diester. This diester is then reacted with an appropriate acid halide or anhydride to give the corresponding 8-ester. The two protecting groups are then readily removed by conversion of the two dibromomethyl groups to formyl (using silver perchlorate and 2,4,6-collidine in aqueous acetone) followed by hydrolysis of the formylbenzoic acid ester obtained using morpholine and hydroxide ion.

The indicated procedure can be used in a similar way to give diester isomers.

With 1,8-O-isopropylidenecastanospermine or 1,8-cyclohexylidenecastanospermine, the reaction with an acid chloride in a standard esterification procedure favors the formation of the 6-ester almost exclusively. The isopropylidene or cyclohexylidene group is then removed by treatment with an acid such as 4-toluenesulphonic acid. The starting ketal compounds are themselves obtained form castanospermine 6,7-dibenzoate. This dibenzoate is reacted with 2-methoxypropene or 1-methoxycyclohexene and acid to introduce the 1,8-O-isopropylidene or 1,8-O-cyclohexylidene group and the two benzoate ester groups are removed by hydrolysis with base such as sodium hydroxide or by transesterification with sodium or potassium alkoxide as the catalyst.

Medical Applications

The invention finds application in medicine, for example in methods of therapy and/or prophylaxis. The methods include veterinary applications.

As used herein, the term "a method of treating *flavivirus* infection" refers to the treatment of a patient (human or animal) which has been infected with a flavivurus. The methods of treatment involve administering to said patient an antivirally effective amount of the compositions or medicaments of the invention.

As used herein, the term "flaviviral infection" refers to any state or condition that involves (e.g. is caused, exacerbated or characterized by) a flavivirus residing in the cells or body of said patient.

The term "patient" used herein is taken to mean mammals such as primates, including humans, sheep, horses, cattle, pigs, dogs, cats, rats and mice.

Posology

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

The amount of the castanospermine ester administered can vary widely according to the particular dosage unit employed, the period of treatment, the age and sex of the patient treated, the nature and extent of the disorder treated, and the particular castanospermine ester selected.

Moreover, the castanospermine ester can be used in conjunction with other agents known to be useful in the treatment of flaviviral infections (as described above) and in such embodiments the dose may be adjusted accordingly.

Lower doses may be used in embodiments that incorporate the castanospermine ester pro-drug derivatives of the invention which exhibit greater resistance to hydrolysis and increased lipophilicity. As explained above, such pro-drugs exhibit rapid removal from the GI tract when delivered orally whilst providing a "depot effect" which sustains the concentration of the active drug at the target site (e.g. the liver).

Thus, the effective amount of castanospermine ester to be administered will generally range from about 15 mg/kg to 500 mg/kg. A unit dosage may contain from 25 to 500 mg of the castanospermine ester, and can be taken one or more times per day. The castanospermine ester can be administered with a pharmaceutical carrier using conventional dosage unit forms either orally, parenterally, or topically, as described below.

The preferred route of administration is oral administration. In general a suitable dose will be in the range of 0.1 to 300 mg per kilogram body weight of the recipient per day, preferably in the range of 6 to 150 mg per kilogram body weight per day and most preferably in the range 15 to 100 mg per kilogram body weight per day.

The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Formulation

The compositions of the invention may be provided in combination with a pharmaceutically acceptable excipient. Any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

The pharmaceutical compositions may take any suitable form, and include for example tablets, elixirs, capsules, solutions, suspensions, powders, granules and aerosols.

The pharmaceutical composition may take the form of a kit of parts, which kit may comprise the composition of the invention together with instructions for use and/or a plurality of different components in unit dosage form.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, d present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity.

Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

For oral administration the castanospermine ester can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The castanospermine ester derivatives of this invention may also be administered parenterally, that is, subcutaneously, intravenously, intramuscularly, or interperitoneally.

In such embodiments, the medicament is provided as injectable doses of the compound in a physiologically acceptable diluent with a pharmaceutical carrier which can be a sterile liquid or mixture of liquids. Suitable liquids include water, saline, aqueous dextrose and related sugar solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carhomers, methylcellulose, hydroxypropylmethylcellulose, or carboxymethylcelluiose), or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil.

Suitable fatty acids include oleic acid, stearic acid, and Isostearic acid. Suitable fatty acid esters are, for example, ethyl oleate and isopropyl myristate.

Suitable soaps Include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quartemary ammonium salts, as well as mixtures.

The parenteral compositions of this Invention will typically contain from about 0.5 to about 25% by weight of the castanospermine ester derivative of formula 1 in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactantcan be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The castanospermine ester derivatives of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the castanospermine ester or it's pharmaceutical salt from about 0.1 to about 10% w/v (weight per unit volume).

The invention will now be described with reference to the following exemplary embodiments, which are purely illustrative and not intended to be limiting in any way. It will be appreciated that modifications to detail may be made whilst still falling within the scope of the invention.

EXAMPLIFICATION

Cells, Virus and Inhibitors

MDBK cells (NBL-1) (ATCC CCL22) derived from bovine kidney and cytopathic (cp) BVDV (strain NADL) (ATCC VR-534) were available from the American Type Culture Collection (ATCC).

MDBK cells were maintained in Dulbecco Modified Eagle Medium (DMEM) (Sigma, Poole, Dorset) supplemented with 10% FCS, 2 mM L-glutamine, 50 U/ml penicillin and 50 μg/ml streptomycin.

60-butanoylcastanospermine (Bucast; Celgosivir; VIR-222; MDL 28,574A) was synthesised as previously described (Liu, P. S., Hoekstra, W. J. and King, C. H. R. (1990). Synthesis of potent anti-HIV agents: esters of castanospermine. Tetrahedron Lett. 31: 1535-1549) and provided by Aventis (previously known as Marion Merrell Dow). Castanospermine (1S, 6S, 7R, 8R, 8aR-1 6, 7, 8 tetrahydroxyindolizidine) isolated from seeds of the Moreton Bay Chestnut, *Castanospermum australe*, as previously described (Liu, P. S. and Rhinehart, B. L. (1986). Isolation of castanospermine and its use as an anti-diabetic agent. Eur. Patent EP 0202661) and was also obtained from Aventis. N-butyl-deoxynojirimycin (N-butyl-DNJ) and N-nonyl-deoxynojirimycin (NN-DNJ) were purchased from Toronto Research Chemicals, Canada. Bucast, Castanospermine and N-butyl-DNJ were made up as 100 mM stock solutions in water. NN-DNJ was made up as a 100 mM stock solution in DMSO. Stock solutions were store at −20° C.

Plaque Reduction Assay

MDBK cells were seeded into 6-well cell culture plates (Nunclon™, Nunc, Denmark) and allowed to grow to confluency. The cells are washed twice in warm phosphate buffered saline (PBS) and then infected with BVDV NADL (150 pfu/well) in 0.25 ml PBS containing 1% horse serum and 1 mM $MgCl_2$. The cell culture plates were then incubated at 37° C. for one hour with 5% $CO_2$ and the plates rocked every 15-20 minutes. The virus inoculum was then removed and replaced with 3.0 ml of 0.5% low-gelling temperature agarose overlay diluted in DMEM supplemented with 5% horse serum, 2 mM L-glutamine, 50 U/ml penicillin and 50 Lg/ml streptomycin and containing different concentrations of test compound or no compound. At least duplicate or triplicate wells were used for each concentration of test compound. The agarose was allowed to solidify at room temperature for 15 minutes and then incubated at 37° C. with 5% $CO_2$. After 3 days incubation the cells were fixed by adding 1.5 ml of a 100% formaldehyde solution over the agar overlay and leaving overnight. The agar was gently removed from the wells and the cells stained with 0.3% methylene blue in PBS for 10 minutes at room temperature. The excess stain was removed and the cells washed with PBS prior to drying of the plates and counting of the viral plaques microscopically. Dose response lines were plotted from the mean number of plaques present versus the log of the concentration of the compound. The 50% Inhibitory concentration ($IC_{50}$) was computed after linear regression analysis.

XTT CytoPathicity Assay

MDBK cells were seeded into 96-well cell culture plates (Costar® 3596, Corning Incorp., USA) and allowed to grow to confluency. The cells were washed twice in warm phosphate buffered saline (PBS) and then infected with BVDV NADL (100 pfu/well) in 100 μl of DMEM supplemented with 5% horse serum, 2 mM L-glutamine, 50 U/ml penicillin and 50 μg/ml streptomycin. Some wells were mock infected to act as controls. A further 100 μl of DMEM supplemented as above, but containing different concentrations of test compound or no compound was then added to each well. Triplicate wells were used for each compound concentration. In parallel, uninfected cells were treated with compound to assess cytotoxicity. The plates were then incubated at 37° C. with 5% $CO_2$. After 6 days 25 μl of a 1 mg/ml 2,3-bis[2-methoxy-4-nitro-5-sulphophenyl]-2H-tetrazolium-5-carboxanilide (XTT)/25 μM phenazine methosulphate (PMS) solution (XTT and PMS purchased from Sigma, Poole, Dorset, UK) was then added to each well and the plates incubated for 2 hours at 37° C. with 5% $CO_2$. The absorbance was then determined at 450 nm. Data was plotted as O. D versus the log of the concentration of the compound and the 50% inhibitory concentration ($IC_{50}$) computed.

Anti-viral Activity

Figure 1:
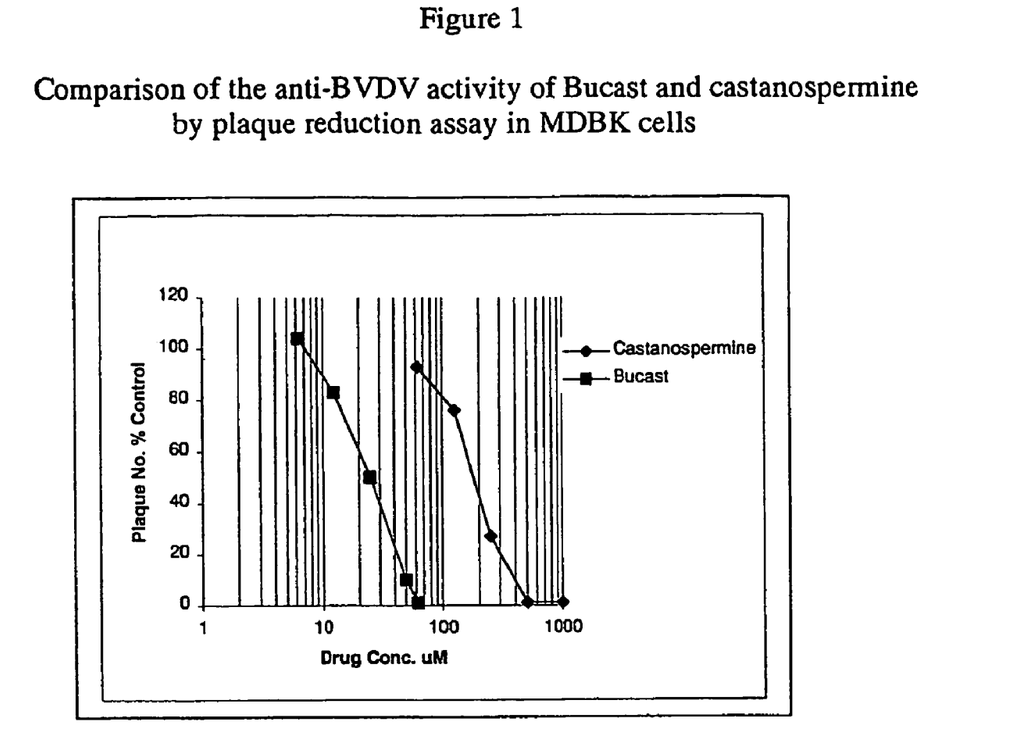
FIG. 1 is a chart depicting the comparison of the anti-BVDV activity of Bucast and castanospermine by plaque reduction assay in MDBK cells.

Using a plaque reduction assay in MDBK cells, both castanospermine and Bucast inhibited the formation of BVDV plaques in a dose dependent manner (see FIG. 1). Bucast was approximately 13 times more potent than castanospermine, as recorded previously with respect to activity against the human immunodeficiency virus (HIV). The mean $IC_{50}$ for Bucast was 16.25 μM ±7.5 μM, compared with a mean $IC_{50}$ of 216.6 μM ±55.0 μM for castanospermine (Table 2).

TABLE 2

Anti-BVDV activity of α-glucosidase I inhibitors determined by plaque reduction assay

| Compound | $IC_{50}$ (μM) | Mean $IC_{50}$ (μM) ± SD | $CC_{50}$ (μM) |
|---|---|---|---|
| Bucast | 10, 10, 20, 25 | 16.25 ± 7.5 | >1000 |
| Castanospermine | 180, 190, 280 | 216.6 ± 55.0 | >1000 |
| N-Butyl-DNJ | >300, 250 | | >300 |
| N-Nonyl-DNJ | 90, 120 | 105 | Toxic @ 300 |

There was no sign of cytotoxicity at concentrations up to 1000 μM as judged by microscopic examination of the cell monolayers. In parallel plaque reduction experiments, the α-glucosidase I inhibitors N-butyl-DNJ and N-nony1-DNJ only showed partial inhibition at concentrations>100 μM and >300 μM, respectively. N-nonyl-DNJ was clearly cytotoxic to cells at a concentration of 300 μM.

Figure 2A:
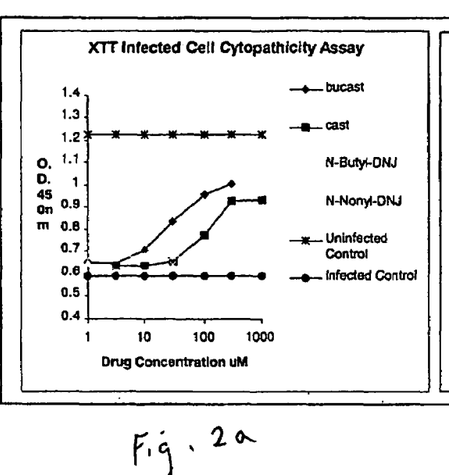
FIG. 2a is a chart depicting anti-BVDV activity and cytotoxicity of α-glucosidase I inhibitors determined by XTT infected cell cytopathicity assay.
Figure 2B:
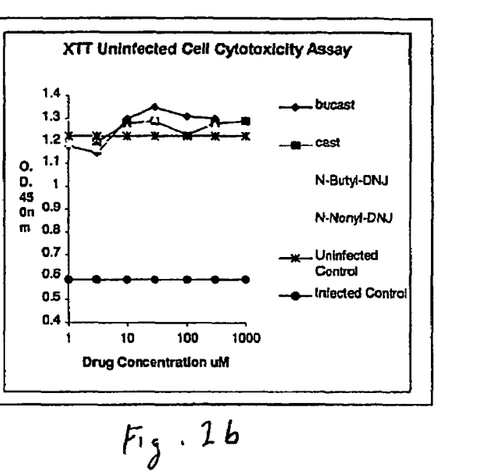
FIG. 2b is a chart depicting anti-BVDV activity and cytotoxicity of α-glucosidase I inhibitors determined by XTT uninfected cell cytopathicity assay.

Similar results were obtained when an XTT cytopathicity assay was used to determine the anti-BVDV effects and cytotoxicity of the α-glucosidase I inhibitors in parallel. As shown in FIG. 2 both Bucast and castanospermine protected MDBK cells against virus-induced cell death whilst showing no cytotoxicity to uninfected treated cells. In the same experiments neither N-butyl-DNJ or N-nonyl-DNJ demonstrated any protection against the cytopathic effect of BVDV. Whilst N-butyl-DNJ showed no cytotoxicity, as observed previously in plaque reduction experiments, N-nonyl-DNJ was clearly cytotoxic to MDBK cells. The calculated 50% cytotoxic concentration of N-nonyl-DNJ was 120 CM. Using a multiplicity of infection (MOI) of approximately 0.01, the mean $IC_{50}$ values for Bucast and castanospermine in this cytopathicity assay were 36 μM ±22 μM and 400 μM respectively (Table 3).

TABLE 3

Anti-BVDV activity and cytotoxicity of α-glucosidase I
inhibitors determined by XTT cytopathicity assay

| Compound | *IC$_{50}$ (μM) | CC$_{50}$ (μM) |
|---|---|---|
| Bucast | 60, 30, 70, 40, 60 mean = 52 ± 16.43 | >300 |
| Castanospermine | 300, 500 mean = 400 | >1000 |
| N-Butyl-DNJ | >300, >1000 | >1000 |
| N-Nonyl-DNJ | 60, >100 | 120 |

*MOI = 0.01

In one experiment, N-nonyl-DNJ showed some antiviral activity, but the selectivity index was only 2-fold.

Figure 3:
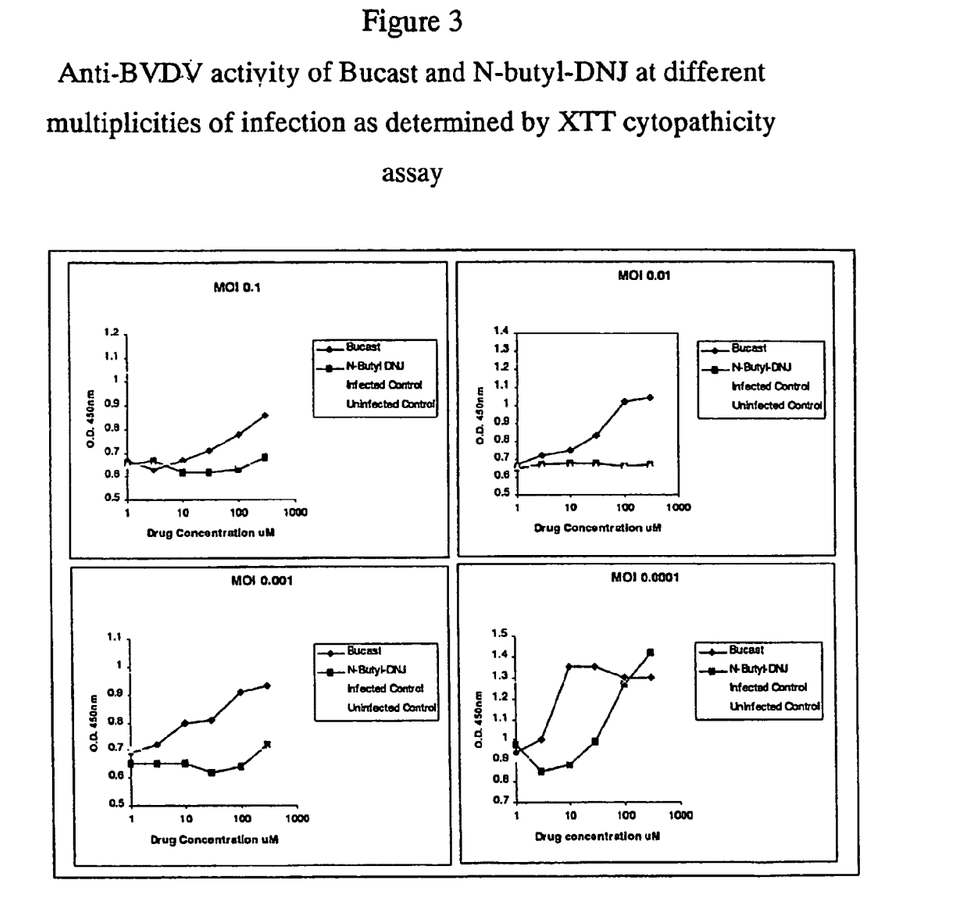
FIG. 3 is a chart depicting anti-BVDV activity of Bucat and N-butyl-DNJ at different multiplicities of infection as determined by XTT cytopathicity assay.

Investigation of the effect of virus MOI on the anti-BVDV activity of Bucast indicated that it was more potent when lower ratios of infectious virus:cell number were used (see FIG. 3 and Table 4).

TABLE 4

Anti-BVDV activity of Bucast and N-Butyl-DNJ at
different multiplicities of infection as determined
by XTT cytopathicity assay

| | IC$_{50}$ (μM) | |
|---|---|---|
| MOI | Bucast | N-Butyl-DNJ |
| 0.1 | 200, 170 | >300 |
| 0.01 | 60, 30 | >300 |
| 0.001 | 40 | >300 |
| 0.0001 | 5.0 | 55 |

Some antiviral effect could be obtained with N-butyl-DNJ when a very low MOI was used, but this inhibitor was 10-fold less potent than Bucast.

The XTT cytopathicity assay was used to assess the ability of human leukocyte interferon (interferon α) to inhibit the cytopathic effect of BVDV on MDBK cells and an IC$_{50}$ value of 1.3 interferon resistance units (IRU) per well was demonstrated. Further experiments demonstrated that the IC$_{50}$ value for interferon a was reduced in the presence of Bucast and interferon a in combination. Also the IC$_{50}$ value for Bucast was reduced using this combination. The combination indexes (CI) were calculated using the formula of Suhnel (Antiviral Research, 13, 23-40). A CI value of less than 1 indicates a synergistic interaction and values of less than 0.8 are considered to indicate a statistically significant result. The combination of interferon a and Bucast produced CI values ranging from 0.28 to 0.46. These results therefore indicate a synergistic effect when Bucast is used in the presence of interferon α.

These data are summarised in Table 5.

TABLE 5

Anti BVDV activity of Bucast in combination with interferon
alpha as determined by XTT cytopathicity assay

| Fixed Drug Concentration Interferon α (IRU/well) | IC$_{50}$ Bucast (μM) | Combination Index (CI) |
|---|---|---|
| 0.5 | 3 | 0.46 |
| 0.25 | 4 | 0.28 |
| 0.125 | 13 | 0.37 |
| 0 | 52 ± 16.43 | |

| Bucast (μM) | Interferon α (IRU/well) | |
|---|---|---|
| 10 | 0.12 | 0.3 |
| 5 | 0.22 | 0.28 |
| 0 | 1.3 | |

Equivalents

The foregoing descriptions detail presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method for treating a *Hepacivirus* infection, said method comprising the step of administering to a patient a therapeutic composition comprising (i) an agent that alters immune function, and (ii) a glucosidase inhibitor wherein the agent that alters immune function is an interferon and the glucosidase inhibitor is [1S-(1α,6β,7α,8β,8αβ)]-octahydro-1 6,7,8-indolizinetetrol 6-butanoate.

2. The method according to claim 1 wherein the patient is a human.

3. The method according to claim 1 wherein the interferon is an α-interferon.

4. The method according to claim 1 wherein said *Hepacivirus* is Hepatitis C virus.

5. The method according to claim 1 wherein the composition further comprises a pharmaceutically acceptable excipient.

6. A method for treating a *Hepacivirus* infection, said method comprising the step of administering to a patient a therapeutic composition comprising (i) an agent that alters viral replication, and (ii) a glucosidase inhibitor wherein the agent that alters replication is ribavirin and the glucosidase inhibitor is [1S-(1α,6β,7α,8β,8αβ)]-octahydro-1 6,7,8-indolizinetetrol 6-butanoate.

7. The method according to claim 6 wherein the patient is a human.

8. The method according to claim 6 wherein said *Hepacivirus* is Hepatitis C virus.

9. The method according to claim 6 wherein the composition further comprises a pharmaceutically acceptable excipient.

10. A method for treating a *Hepacivirus* infection, said method comprising the step of administering to a patient a therapeutic composition comprising a glucosidase inhibitor, wherein the glucosidase inhibitor is [1S-(1α,6β,7α,8β,8αβ)]-octahydro-1 6,7,8-indolizinetetrol 6-butanoate.

11. The method according to claim 10 wherein said *Hepacivirus* is Hepatitis C virus.

12. The method according to claim 10 wherein the composition further comprises a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,601,735 B2 | Page 1 of 1 |
| APPLICATION NO. | : 10/475830 | |
| DATED | : October 13, 2009 | |
| INVENTOR(S) | : Tyms et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1318 days.

Signed and Sealed this

Fourteenth Day of December, 2010

David J. Kappos
*Director of the United States Patent and Trademark Office*